United States Patent
Beller

(10) Patent No.: US 10,913,935 B2
(45) Date of Patent: *Feb. 9, 2021

(54) MODIFIED BACTERIUM USEFUL FOR PRODUCING AN ORGANIC MOLECULE

(71) Applicant: Harry R. Beller, Berkeley, CA (US)

(72) Inventor: Harry R. Beller, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/216,929

(22) Filed: Mar. 17, 2014

(65) Prior Publication Data

US 2015/0184133 A1 Jul. 2, 2015

Related U.S. Application Data

(60) Provisional application No. 61/793,430, filed on Mar. 15, 2013.

(51) Int. Cl.

| | | |
|---|---|---|
| *C12N 9/02* | (2006.01) | |
| *C12P 7/64* | (2006.01) | |
| *C12P 7/26* | (2006.01) | |
| *C02F 3/34* | (2006.01) | |
| *C12N 1/32* | (2006.01) | |
| *C02F 3/28* | (2006.01) | |
| *C12N 9/16* | (2006.01) | |
| *C02F 101/16* | (2006.01) | |
| *C02F 101/10* | (2006.01) | |
| *C02F 103/36* | (2006.01) | |
| *C02F 101/32* | (2006.01) | |

(52) U.S. Cl.
CPC ............... *C12N 9/001* (2013.01); *C02F 3/28* (2013.01); *C02F 3/342* (2013.01); *C02F 3/345* (2013.01); *C12N 1/32* (2013.01); *C12N 9/16* (2013.01); *C12P 7/26* (2013.01); *C12P 7/6409* (2013.01); *C12Y 103/03006* (2013.01); *C02F 2101/101* (2013.01); *C02F 2101/163* (2013.01); *C02F 2101/32* (2013.01); *C02F 2103/36* (2013.01); *C02F 2303/08* (2013.01)

(58) Field of Classification Search
None
See application file for complete search history.

(56) References Cited

U.S. PATENT DOCUMENTS

2010/0120104 A1* 5/2010 Reed ..................... C12N 1/20
  435/140
2012/0064622 A1* 3/2012 Fischer .................. C12P 5/00
  435/348
2013/0059295 A1  3/2013 Zhang et al.

FOREIGN PATENT DOCUMENTS

| WO | 2009/006430 A1 | 1/2009 |
| WO | 2010/127318 A2 | 11/2010 |
| WO | 2013/063513 A1 | 5/2013 |

OTHER PUBLICATIONS

Steen et al., Microbial production of fatty-acid-derived fuels and chemicals from plant biomass, Nature, Jan. 28, 2010, vol. 463(7280), pp. 559-562.*
Stewart et al., Periplasmic Nitrate Reductase (NapABC Enzyme) Supports Anaerobic Respiration by *Escherichia coli* K-12. J Bacteriol. Mar. 2002; 184(5): 1314-1323.*
Letain et al., Development of a Genetic System for the Chemolithoautotrophic Bacterium Thiobacillus denitrificans., Appl. Environ. Microbiol. May 2007, vol. 73, No. 10, pp. 3265-3271.*
The Mycota., A comprehensive Treaties on Fungi as Experimental Ssytems for Basic and Applied Research, 1995, Ed. K. Esser and P.A. Lemke, p. 117.*
Wright et al., Aminoglycoside Phosphotransferase: Proteins, Structure, and Mechanism., Frontiers in Bioscience (1999), vol. 4, pp. 9-21.*
Beller et al., "The Genome Sequence of the Obligately Chemolithoautotrophic, Facultatively Anaerobic Bacterium Thiobacillus denitrificans," J. Bacteriol. 188:1473-1488 (2006).
Beller et al., "Whole-Genome Transcriptional Analysis of Chemolithoautotrophic Thiosulfate Oxidation by Thiobacillus denitrificans under Aerobic versus Denitrifying Conditions," J. Bacteriol. 188:7005-7015 (2006).
Beller et al., "Genetic manipulation of the obligate chemolithoautotrophic bacterium Thiobacillus denitrificans", vol. 881, pp. 99-136, In Microbial Systems Biology: Methods and Protocols [Methods in Molecular Biology series], A. Navid (ed.), Springer Science. DOI 10.1007/978-1-61779-827-6_5. (2012).
Goh et al., "Engineering of bacterial methyl ketone synthesis for biofuels." Appl. Environ. Microbiol. 78:70-80. (2012).

* cited by examiner

*Primary Examiner* — Iqbal H Chowdhury
(74) *Attorney, Agent, or Firm* — Robin C. Chiang; Lawrence Berkeley National Laboratory

(57) ABSTRACT

The present invention provides for a genetically modified host cell or bacterium capable of producing an organic molecule, wherein the bacterium is capable of using hydrogen sulfide as an electron donor, carbon dioxide ($CO_2$) as a carbon source, and/or nitrate as an electron acceptor. The present invention is useful in the wastewater treatment industry, in particular in municipal wastewater treatment plants (WWTP).

16 Claims, No Drawings

Specification includes a Sequence Listing.

MODIFIED BACTERIUM USEFUL FOR PRODUCING AN ORGANIC MOLECULE

CROSS-REFERENCE TO RELATED APPLICATIONS

This application claims priority to U.S. Provisional Patent Application Ser. No. 61/793,430, filed Mar. 15, 2013.

STATEMENT OF GOVERNMENTAL SUPPORT

The invention described and claimed herein was made utilizing funds supplied by the U.S. Department of Energy under Contract No. DE-AC02-05CH11231. The government has certain rights in this invention.

FIELD OF THE INVENTION

The present invention is in the field of bioremediation.

BACKGROUND OF THE INVENTION

There are existing chemical and biological techniques in using certain bacteria to remove sulfide and/or nitrate from wastewater, but there are no teachings regarding combining chemolithoautotrophic sulfide oxidation with biofuel/biobased chemical production. There is no existing technology to produce carbon-neutral (i.e., $CO_2$-derived) biofuels/bio-based chemicals using hydrogen sulfide as an electron donor (energy source).

SUMMARY OF THE INVENTION

The present invention provides for a genetically modified host cell or bacterium capable of producing an organic molecule, wherein the bacterium is capable of using hydrogen sulfide as an electron donor, carbon dioxide ($CO_2$) as a carbon source, and/or nitrate as an electron acceptor. The bacterium comprises the genes encoding the enzymes for using hydrogen sulfide as an electron donor, carbon dioxide ($CO_2$) as a carbon source, and nitrate as an electron acceptor. In some embodiments, the bacterium produces an organic molecule that the unmodified bacterium does not produce. In some embodiments, the bacterium is a chemolithoautotroph. In some embodiments, the bacterium is an obligate chemolithoautotroph. In some embodiments, the bacterium uses hydrogen sulfide as a sole electron donor and/or $CO_2$ as a sole carbon source. In some embodiments, the bacterium is a species from the genera *Thiobacillus, Thiomicrospira, Sulfurimonas, Thioalkalivibrio*, or *Sulfurovum*. In some embodiments, the organic molecule is a biofuel. In some embodiments, the organic molecule is a fatty acid or a methyl ketone.

The present invention also provides for a method of growing a host cell or bacterium of the present invention, comprising: (a) providing the host cell or bacterium, and (b) culturing the host cell or bacterium in a liquid comprising hydrogen sulfide and $CO_2$, and optionally nitrate, whereby optionally the bacterium produces an organic molecule that the unmodified bacterium does not produce or overproduces the organic molecule when compared to an unmodified host cell or bacterium.

The present invention is useful in the wastewater treatment industry, in particular in municipal wastewater treatment plants (WWTP). In some embodiments, the bacterium is useful in any wastewater that is rich or elevated in hydrogen sulfide, such as in certain petroleum waste streams. In some embodiments, the municipal WWTP is high in sulfide, nitrate, and/or $CO_2$ content.

DETAILED DESCRIPTION OF THE INVENTION

Before the invention is described in detail, it is to be understood that, unless otherwise indicated, this invention is not limited to particular sequences, expression vectors, synthetic TF, host microorganisms, or processes, as such may vary. It is also to be understood that the terminology used herein is for purposes of describing particular embodiments only, and is not intended to be limiting.

As used in the specification and the appended claims, the singular forms "a," "an," and "the" include plural referents unless the context clearly dictates otherwise. Thus, for example, reference to an "expression vector" includes a single expression vector as well as a plurality of expression vectors, either the same (e.g., the same operon) or different; reference to "cell" includes a single cell as well as a plurality of cells; and the like.

In this specification and in the claims that follow, reference will be made to a number of terms that shall be defined to have the following meanings:

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

The terms "host cell" and "bacterium" are used interchangeably herein to refer to a living bacterial cell that can be transformed via insertion of an expression vector.

The term "heterologous" as used herein refers to a molecule, compound, protein, or enzyme that is not naturally found in a species. The term "heterologous DNA" as used herein refers to a polymer of nucleic acids wherein at least one of the following is true: (a) the sequence of nucleic acids is foreign to (i.e., not naturally found in) a given host microorganism; (b) the sequence may be naturally found in a given host microorganism, but in an unnatural (e.g., greater than expected) amount; or (c) the sequence of nucleic acids comprises two or more subsequences that are not found in the same relationship to each other in nature. For example, regarding instance (c), a heterologous nucleic acid sequence that is recombinantly produced will have two or more sequences from unrelated genes arranged to make a new functional nucleic acid. Specifically, the present invention describes the introduction of an expression vector into a host microorganism, wherein the expression vector contains a nucleic acid sequence coding for peptides and proteins that is not normally found in a host microorganism. With reference to the host microorganism's genome, then, the nucleic acid sequence that codes for the peptides and proteins is heterologous.

The terms "expression vector" or "vector" refer to a compound and/or composition that transduces, transforms, or infects a host cell, thereby causing the cell to express nucleic acids and/or proteins other than those native to the cell, or in a manner not native to the cell. An "expression vector" contains a sequence of nucleic acids (ordinarily RNA or DNA) to be expressed by the host cell. Optionally, the expression vector also comprises materials to aid in achieving entry of the nucleic acid into the host cell, such as a virus, liposome, protein coating, or the like. The expression vectors contemplated for use in the present invention include those into which a nucleic acid sequence can be inserted, along with any preferred or required operational elements. Further, the expression vector must be one that can be transferred into a host cell and replicated therein. Particular expression vectors are plasmids, particularly those with restriction sites that have been well documented and that contain the operational elements preferred or required for transcription of the nucleic acid sequence. Such plasmids, as well as other expression vectors, are well known to those of ordinary skill in the art.

The term "transduce" as used herein refers to the transfer of a sequence of nucleic acids into a host cell. Only when the sequence of nucleic acids becomes stably replicated by the cell does the host cell become "transformed." As will be appreciated by those of ordinary skill in the art, "transformation" may take place either by incorporation of the sequence of nucleic acids into the cellular genome, i.e., chromosomal integration, or by extrachromosomal integration. In contrast, an expression vector, e.g., a virus, is "infective" when it transduces a host cell, replicates, and (without the benefit of any complementary virus or vector) spreads progeny expression vectors, e.g., viruses, of the same type as the original transducing expression vector to other microorganisms or cells, wherein the progeny expression vectors possess the same ability to reproduce.

As used herein, the terms "nucleic acid sequence," "sequence of nucleic acids," and variations thereof shall be generic to polydeoxyribonucleotides (containing 2-deoxy-D-ribose), to polyribonucleotides (containing D-ribose), to any other type of polynucleotide that is an N-glycoside of a purine or pyrimidine base, and to other polymers containing nonnucleotidic backbones, provided that the polymers contain nucleobases in a configuration that allows for base pairing and base stacking, as found in DNA and RNA. Thus, these terms include known types of nucleic acid sequence modifications, for example, substitution of one or more of the naturally occurring nucleotides with an analog; internucleotide modifications, such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., arninoalklyphosphoramidates, aminoalkylphosphotriesters); those containing pendant moieties, such as, for example, proteins (including nucleases, toxins, antibodies, signal peptides, poly-L-lysine, etc.); those with intercalators (e.g., acridine, psoralen, etc.); and those containing chelators (e.g., metals, radioactive metals, boron, oxidative metals, etc.). As used herein, the symbols for nucleotides and polynucleotides are those recommended by the IUPAC-IUB Commission of Biochemical Nomenclature (*Biochem.* 9:4022, 1970).

The term "operably linked" refers to a functional linkage between a nucleic acid expression control sequence (such as a promoter) and a second nucleic acid sequence, wherein the expression control sequence directs transcription of the nucleic acid corresponding to the second sequence.

The present invention provides for a genetically modified bacterium capable of producing a heterologous chemical, wherein the bacterium is capable of using hydrogen sulfide as an electron donor, carbon dioxide ($CO_2$) as a carbon source, and nitrate as an electron acceptor. The bacterium comprises the genes encoding the enzymes for using hydrogen sulfide as an electron donor, carbon dioxide ($CO_2$) as a carbon source, and nitrate as an electron acceptor. In some embodiments, the bacterium produces an organic molecule that the unmodified bacterium does not produce. In some embodiments, the bacterium is a chemolithoautotroph. In some embodiments, the bacterium is an obligate chemolithoautotroph. In some embodiments, the bacterium uses hydrogen sulfide as a sole electron donor and/or $CO_2$ as a sole carbon source. In some embodiments, the bacterium is a species from the genera *Thiobacillus, Thiomicrospira, Sulfurimonas, Thioalkalivibrio*, or *Sulfurovum*. In some embodiments, the bacterium is a *Thiobacillus denitrificans*. In some embodiments, the bacterium is a *Sulfurimonas denbrificans*. In some embodiments, the organic molecule is a biofuel. In some embodiments, the organic molecule is a fatty acid or a methyl ketone.

*Thiobacillus denbrificans* is commercially available from the American Type Culture Collection (ATCC; Manassas, Va.) (ATCC 25259).

*Sulfurimonas denbrificans* is commercially available from the American Type Culture Collection (ATCC; Manassas, Va.) (ATCC 33889).

In some embodiments, the bacterium is useful in wastewater (environmental) engineering, metabolic engineering, and/or production of biofuels/biobased chemicals. In some embodiments, the bacterium is an engineered chemolithoautotrophic bacterium (such as *Thiobacillus denitrificans*) capable of removing hydrogen sulfide, carbon dioxide, and optionally nitrate from its environment, such as a waste stream (such as a municipal wastewater), and optionally producing an organic molecule, such as a biofuel or biobased chemical, using the metabolic energy derived from sulfide oxidation and the carbon derived from $CO_2$ fixation.

In some embodiments, the bacterium is useful in a wastewater treatment process that converts problematic chemicals in wastewater streams (sulfide, nitrate, and/or $CO_2$) into harmless or useful compounds in a sustainable manner (e.g., without requiring addition of exogenous energy or materials). In the process, hydrogen sulfide (a corrosive, toxic, and odorous compound that damages piping in sewage treatment plants and in plants treating petroleum-based wastewater) is oxidized to sulfate, nitrate, and/or nitrite (which may be present in municipal wastewater streams, especially those that use nitrification/denitrification to remove ammonium) are reduced to nitrogen gas ($N_2$), and $CO_2$ (a greenhouse gas) is converted to biofuels/biobased chemicals and microbial cells.

There are existing chemical and biological techniques to remove sulfide and/or nitrate from wastewater, even using *Thiobacillus denitrificans* (at least in bench- or pilot-scale studies), but there have been no efforts to combine chemolithoautotrophic sulfide oxidation with biofuel/biobased chemical production (in *Thiobacillus denitrificans* or in any other bacterium). Some advantages of the proposed invention over existing technologies include the following: using the energy from sulfide oxidation and the carbon from $CO_2$ to make biofuels/biobased chemicals; compared to heterotrophic denitrification as a means of removing nitrate, chemolithoautotrophic denitrification (driven by sulfide) requires no addition of an organic electron donor (reduced operating costs), produces less biomass (less sludge for disposal), and is a sink for $CO_2$ (reduced greenhouse gases).

Methods to modify the host cell, such as *Thiobacillus denitrificans*, are known in the art. Such methods are taught in Beller et al., 2006, J. Bacteriol. 188:1473-1488; Beller et al., 2006, J. Bacteriol. 188:7005-7015); and, Letain et al., 2007, Appl. Environ. Microbiol. 73:3265-3271; which are hereby incorporated by reference.

The present invention is useful in the wastewater treatment industry, in particular in municipal wastewater treatment plants (WWTP). In some embodiments, the bacterium is useful in any wastewater that is rich or elevated in hydrogen sulfide, such as in certain petroleum waste streams. In some embodiments, the municipal WWTP is high in sulfide, nitrate, and/or $CO_2$ content.

In some embodiments, the bacterium is modified or engineered to overproduce a chemical, such as one or more fatty-acid-derived biofuels/bio-based chemicals. In some embodiments, the bacterium is modified or engineered to growing and metabolize anaerobically with wastewater-derived hydrogen sulfide as the sole electron donor, $CO_2$ as the sole carbon source, and nitrate as the electron acceptor. In some embodiments, the bacterium is modified or engineered to overproduce a chemical, such as one or more fatty-acid-derived biofuels/bio-based chemicals, while growing and metabolizing anaerobically with hydrogen sulfide as a sole electron donor, $CO_2$ as a sole carbon source, and nitrate as an electron acceptor. The hydrogen sulfide, $CO_2$, and/or nitrate can be derived from wastewater.

In some embodiments, the genetically modified bacterium is transformed with a nucleic acid construct encoding one or more enzymes that are heterologous to the bacterium wherein the one or more enzymes catalyze one or more reactions which convert a starter molecule naturally produced by the unmodified bacterium into the organic molecule. Each enzyme catalyzes the starter molecule into the organic molecule, the starter molecule into an intermediate, or an/the intermediate into the organic molecule.

In a particular embodiment, the invention process for a method comprising providing the bacterium of the present invention, and culturing the bacterium in a liquid comprising sulfide and $CO_2$, and optionally nitrate, whereby optionally the bacterium produces an organic molecule that the unmodified bacterium does not produce.

In some embodiments, the liquid is a wastewater. In some embodiments, the providing step comprises constructing the host cell or bacterium of the present invention. In some embodiments, the constructing step comprises introducing heterologous nucleic acid encoding the enzymes for using hydrogen sulfide as an electron donor, carbon dioxide ($CO_2$) as a carbon source, and/or nitrate as an electron acceptor into the unmodified bacterium. In some embodiments, the introduced heterologous nucleic acid is capable of stable maintenance in the bacterium. In some embodiments, the enzymes, the genes encoding the enzymes, the promoter operably linked to the genes, and/or sequences necessary for stable maintenance of the nucleic acid in the bacterium are heterologous to the bacterium. In some embodiments, the sulfide is hydrogen sulfide.

In some embodiments, the culturing step results in reducing the amount of sulfide, $CO_2$, and/or nitrate in the liquid. In some embodiments, the culturing step is a continuous culture wherein additional liquid optionally comprising further sulfide, $CO_2$, and/or nitrate is added to the liquid comprising the host cell or bacterium. In some embodiments, the culturing step results in reducing the amount of hydrogen sulfide, $CO_2$, and/or nitrate in the liquid which is equal to or more than the further sulfide, $CO_2$, and/or nitrate in the additional liquid added.

In some embodiments, the method is a wastewater treatment process that converts problematic or unwanted or undesired chemicals in wastewater streams (sulfide, nitrate, $CO_2$) into biofuels/bio-based chemicals and harmless compounds in a sustainable manner (e.g., without requiring addition of exogenous electron donors or acceptors). In the method, hydrogen sulfide (a corrosive, toxic, and malodorous compound that damages piping in sewage treatment plants) is oxidized to sulfate, nitrate and/or nitrite (which may be present in municipal wastewater streams, especially those that use nitrification/denitrification to remove ammonium) is reduced to nitrogen gas ($N_2$), and $CO_2$ (a greenhouse gas) is converted to biofuels/bio-based chemicals and microbial cell material.

In some embodiments, the bacterium is a modified *Thiobacillus denitrificans*, an obligate chemolithoautotrophic bacterium. Tools for genetic manipulation of *T. denitrificans* have been described (Letain et al. 2007; Beller et al. 2012) and could be used for plasmid-based overexpression of target genes (either native or heterologous). Chromosomal integration is also possible using existing methods. In some embodiments, the bacterium is modified to produce or overproduce one or more fatty acids or methyl ketones.

Overproduction of fatty acids could include overexpression of one or more, or all, of the following genes: (a) 'tesA (leaderless version from *E. coli* DH1, optionally codon-optimized)—expression of this cytoplasmically directed thioesterase cleaves acyl-ACP thioesters, thus de-regulating fatty acid biosynthesis (e.g., at acetyl-CoA carboxylase and FabH steps)—this approach has been used successfully in *E. coli*, e.g., Steen et al. (2010); (b) pyruvate kinase and pyruvate dehydrogenase (all 3 subunits) (from *T. denitrificans*): to convert phosphoenolpyruvate (PEP) to acetyl-CoA via pyruvate; ultimately, this should direct the flux of fixed carbon to acetyl-CoA; and (c) acetyl-CoA carboxylase (from *T. denitrificans* or *Corynebacterium glutamicum*) and potentially fabD (from *T. denitrificans*): this should direct flux from acetyl-CoA to malonyl-CoA and ultimately malonyl-ACP, which is an important precursor for fatty acid biosynthesis. Diesel-range aliphatic methyl ketones could serve as biofuels (diesel blending agents) or, for 2-undecanone and 2-tridecanone, as flavor and fragrance chemicals (Goh et al. 2012).

Diesel-range aliphatic methyl ketones could serve as biofuels (diesel blending agents) or, for 2-undecanone and 2-tridecanone, as flavor and fragrance chemicals (Goh et al. 2012). Overexpression of the following genes could lead to overproduction of methyl ketones (as shown in *E. coli*; Goh et al. 2010): (a) acyl-CoA oxidase (Mlut_11700, from *Micrococcus luteus*), (b) fadB (from *E. coli* DH1, codon-optimized), (c) fadM (from *E. coli* DH1, codon-optimized), and (d) fadD (from *E. coli* DH1, codon-optimized)—this enzyme catalyzing the first step of β-oxidation is needed in *T. denitrificans*, which lacks a β-oxidation pathway, but is not needed in *E. coli* (Goh et al. 2012) because the native FadD activity is sufficient.

FadD, acyl-CoA oxidase, and FadB are used to generate a truncated β-oxidation pathway designed to overproduce β-ketoacyl-CoAs. FadM acts as a thioesterase to cleave the β-ketoacyl-CoAs to β-keto acids, which can spontaneously decarboxylate to form methyl ketones.

The expression vectors and/or genes suitable for use in the invention are known in the art, and some are taught in PCT International Patent Application Nos. PCT/US2012/062285, PCT/US2008/068833, PCT/US2010/033299; and U.S. Patent Application Publication No. 2013/0059295 (which are hereby incorporated by reference).

In some embodiments, $O_2$ as an electron acceptor rather than nitrate. This suitable when the wastewater does not contain sufficient nitrate or is not accessed to a nitrate waste stream. Although *T. denitrificans* can grow with sulfide and $O_2$, there are disadvantages to this approach, including: (a) the pH of the medium will decrease much more rapidly under aerobic conditions than under denitrifying conditions, so it will require more buffering, (b) aerobic respiration will require more energy resources for aeration, (c) abiotic sulfide oxidation by $O_2$ will compete with the biological sulfide oxidation, and (d) in general, it is probably more metabolically efficient to make reduced compounds (such as aliphatic methyl ketones) under anaerobic conditions than under aerobic conditions.

In some embodiments, metabolic pathways for biofuels/biobased chemicals could include pathways other than those leading to overproduction of fatty acids, such as isoprenoid pathways (using the native non-mevalonate or 2C-methyl-D-erythritol 4-phosphate/1-deoxy-D-xylulose 5-phosphate (MEP/DOXP) pathway).

In some embodiments, the modified bacterium converts fatty acids to biofuels/bio-based chemicals in vivo, the fatty acids could be harvested as a chemical feedstock and catalytically converted to biofuels, such as aliphatic hydrocarbons, using a chemical catalyst. Such chemical catalysts are known to those skilled in the art.

In some embodiments, in addition to municipal WWTP, this invention could also be applicable to other waste streams that contain substantial hydrogen sulfide loadings, such as wastewater associated with certain petroleum-related processes.

In some embodiments, the invention comprises a process involving a single bacterial species to simultaneously remove hydrogen sulfide, nitrate, and $CO_2$ from a waste stream (such as municipal wastewater) and produce biofuels/bio-based chemicals, such as medium-chain methyl ketones.

In some embodiments, the genetically modified bacterium produces methyl ketones, wherein the genetically modified bacterial host cell is transformed with a heterologous nucleic acid construct encoding a FadM that is capable of converting a β-ketoacyl-CoA to a β-keto acid, wherein the genetically modified host overproduces β-ketoacyl-CoAs. In some embodiments, the FadM is has at least 60% amino acid sequence identity to SEQ ID NO: 1. In some embodiments, the FadM is an E. coli FadM. In some embodiments, the genetically modified bacterium comprises a nucleic acid that encodes an acyl-CoA oxidase capable of converting an acyl-CoA to a trans-2-enoyl-CoA; and does not express FadA. In some embodiments, the acyl-CoA oxidase has at least 60% amino acid sequence identity to SEQ ID NO:2. In some embodiments, the acyl-CoA oxidase is from Micrococcus luteus. In some embodiments, the genetically modified bacterium further comprises a nucleic acid that encodes a FadB capable of convening a trans-2-enoyl-CoA to a β-hydroxyacyl-CoA and a β-hydroxyacyl-CoA to a β-ketoacyl-CoA. In some embodiments, the genetically modified bacterium does not express FadE and comprises a nucleic acid encoding a cytoplasmically-directed thioesterase 'tesA gene. In some embodiments, the genetically modified bacterium does not express poxB. In some embodiments, the genetically modified bacterium overexpresses FadR and FadD. The present invention provides for a method of enhancing production of methyl ketones, the method comprising culturing the genetically modified bacterium under conditions such that the culturing results in the production of methyl ketones. In some embodiments, the method further comprises recovering the methyl ketones using a decane overlay.

E. coli FadM comprises the amino acid sequence as follows (accession number ACX40792.1):

(SEQ ID NO: 1)
MQTQIKVRGYHLDVYQHVNNARYLEFLEEARWDGLENSDSFQWMTAHNIA

FVVVNININYRRPAVLSDLLTITSQLQQLNGKSGILSQVITLEPEGQVVA

DALITFVCIDLKTQKALALEGELREKLEQMVK.

Micrococcus luteus NCTC 2665 acyl-CoA oxidase comprises the amino acid sequence as follows (accession number YP_002957230.1):

(SEQ ID NO: 2)
MTVHEKLAPQSPTHSTEVPTDVAEIAPERPTPGSLDAAALEEALLGRWAA

ERRESRELAKDPALWRDPLLGMDEHRARVLRQLGVLVERNAVHRAFPREF

GGEDNHGGNISAFGDLVLADPSLQIKAGVQWGLFSSAILHLGTAEHHRRW

LPGAMDLSVPGAFAMTEIGHGSDVASIATTATYDEATQEFVIHTPFKGAW

KDYLGNAALHGRAATVFAQLITQGVNHGVHCFYVPIRDEKGAFLPGVGGE

DDGLKGGLNGIDNGRLHFTQVRIPRTNLLRYGDVAEDGTYSSPIASPGRR

FFTMLGTLVQGRVSLSLAATTASFLGLHGALAYAEQRRQFNASDPQREEV

LLDYQNHQRRLIDRLARAYADAFASNELVVKFDDVFSGRSDTDVDRQELE

TLAAAVKPLTTWHALDTLQEAREACGGAGFLAENRVTQMRADLDVYVTFE

GDNTVLLQLVGKRLLTDYSKEFGRLNVGAVSRYVVHQASDAIHRAGLHKA

VQSVADGGSERRSANWFKDPAVQHELLTERVRAKTADVAGTLSGARGKGQ

AAQAEAFNTRQHELIEAARNHGELLQWEAFTRALEGITDETTKTVLTWLR

DLFALRLIEDDLGWFVAHGRVSSQRARALRGYVNRLAERLRPFALELVEA

FGLEPEHLRMAVATDAETQRQEEAHAWFTARRAAGEEPEDEKAVRAREKA

ARGRRG.

In some embodiments, the genetically modified bacterium comprises one or more heterologous nucleic acids encoding one or more of a thioesterase, a fatty acyl-coA synthetase, an acyl-transferase, an alcohol dehydrogenase, a pyruvate decarboxylase. In some embodiments, the genetically modified bacterium comprises an endogenous nucleic acid encoding a fatty acyl-coA dehydrogenase. In some embodiments, the genetically modified bacterium is modified such that expression of the fatty acyl-coA dehydrogenase is attenuated relative to the level of expression in a non-modified cell. In some embodiments, the thioesterase is 'tesA from E. coli. In some embodiments, the fatty acyl-coA synthetase is fadD from E. coli. In some embodiments, the alcohol dehydrogenase is adhB from Zymomomas mobilis. In some embodiments, the pyruvate decarboxylase is pdc from Zymomomas mobilis. In some embodiments, the acyl-transferase is the wax ester synthase atfA from Acinetobacter strain ADP1.

REFERENCES CITED

Beller, H. R., T. C. Legler, and S. R. Kane. 2012 (Book chapter). "Genetic manipulation of the obligate chemolithoautotrophic bacterium Thiobacillus denitrificans", vol. 881, pp. 99-136, In Microbial Systems Biology: Methods and Protocols [Methods in Molecular Biology series], A. Navid (ed.), Springer Science. DOI 10.1007/978-1-61779-827-6_5.

Goh, E.-B., E. E. K. Baidoo, J. D. Keasling, and H. R. Beller. 2012. Engineering of bacterial methyl ketone synthesis for biofuels. *Appl. Environ. Microbiol.* 78:70-80.

Letain, T. E., S. R. Kane, T. C. Legler, E. P. Salazar, P. G. Agron, and H. R. Beller. 2007. Development of a genetic system for the chemolithoautotrophic bacterium *Thiobacillus denitrificans*. *Appl. Environ. Microbiol.* 73:3265-3271.

Steen, E. J., Y. Kang, G. Bokinsky, Z. Hu, A. Schirmer, A. McClure, S. B. del Cardayre, and J. D. Keasling. 2010. Microbial production of fatty acid-derived chemicals from plant biomass. *Nature* 463(7280):559-562.

The references are hereby incorporated by reference.

It is to be understood that, while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

I claim:

1. A genetically modified bacterium capable of producing an organic molecule comprising a heterologous nucleic acid encoding a 'tesA integrated into a chromosome of the genetically modified bacterium, wherein the genetically modified bacterium is capable of using hydrogen sulfide as an electron donor, carbon dioxide ($CO_2$) as a source, and nitrate as an electron acceptor, and the organic molecule is heterologous or the genetically modified bacterium overproduces the organic molecule compared to an unmodified bacterium; wherein the organic molecule is a fatty acid and the genetically modified bacterium is a chemolithoautotroph, wherein the organic molecule is a methyl ketone and the heterologous nucleic acid encodes two or more of acyl-CoA oxidase, FadB, FadM, and FadD.

2. The bacterium of claim 1, wherein the acyl-CoA oxidase a *Micrococcus luteus* acyl-CoA oxidase, and FadB, FadM, and FadD are *Escherichia coli* FadB, FadM, and FadD.

3. The genetically modified bacterium of claim 1, wherein the heterologous nucleic acid encodes one or more of pyruvate kinase and pyruvate dehydrogenase, and acetyl-CoA carboxylase.

4. The genetically modified bacterium of claim 1, wherein the genetically modified bacterium is a species from the genera *Thiobacillus*, *Thiomicrospira*, *Sulfurimonas*, *Thioalkalivibrio*, or *Sulfurovum*.

5. The genetically modified bacterium of claim 4, wherein the genetically modified bacterium is a *Thiobacillus denitrificans*.

6. The bacterium of claim 4, wherein the bacterium is a *Sulfurimonas denitrificans*.

7. The genetically modified bacterium of claim 1 comprising one or more genes encoding enzymes for using hydrogen sulfide as an electron donor, $CO_2$ as a carbon source, and/or nitrate as an electron acceptor.

8. The genetically modified bacterium of claim 7, wherein the genetically modified bacterium uses hydrogen sulfide as a sole electron donor and/or $CO_2$ as a sole carbon source.

9. The genetically modified bacterium of claim 7, wherein the organic molecule is a biofuel.

10. A method of growing the genetically modified bacterium of claim 1, comprising:
    (a) providing the genetically modified bacterium of claim 1, and
    (b) culturing the genetically modified bacterium in a liquid comprising hydrogen sulfide and $CO_2$, and optionally nitrate,
        whereby optionally the genetically modified bacterium produces the organic molecule that the genetically unmodified bacterium does not produce or overproduces the organic molecule when compared to an unmodified bacterium.

11. The method of claim 10, wherein the liquid is a wastewater.

12. The method of claim 10, wherein the providing step comprises constructing the genetically modified bacterium.

13. The method of claim 12, wherein the constructing step comprises introducing heterologous nucleic acid encoding one or more enzymes for using sulfide as an electron donor, carbon dioxide ($CO_2$) as a carbon source, and/or nitrate as an electron acceptor into an unmodified bacterium.

14. The method of claim 13, wherein the introduced heterologous nucleic acid is capable of stable maintenance in the genetically modified bacterium.

15. The method of claim 10, wherein the culturing step results in reducing the amount of hydrogen sulfide, $CO_2$, and/or nitrate in the liquid.

16. The method of claim 10, wherein the culturing step is a continuous culture wherein additional liquid optionally comprising further hydrogen sulfide, $CO_2$, and/or nitrate is added to the liquid comprising the genetically modified bacterium.

\* \* \* \* \*

```
                        SEQUENCE LISTING

<160> NUMBER OF SEQ ID NOS: 2

<210> SEQ ID NO 1
<211> LENGTH: 132
<212> TYPE: PRT
<213> ORGANISM: Escherichia coli

<400> SEQUENCE: 1

Met Gln Thr Gln Ile Lys Val Arg Gly Tyr His Leu Asp Val Tyr Gln
1               5                   10                  15

His Val Asn Asn Ala Arg Tyr Leu Glu Phe Leu Glu Glu Ala Arg Trp
            20                  25                  30

Asp Gly Leu Glu Asn Ser Asp Ser Phe Gln Trp Met Thr Ala His Asn
        35                  40                  45

Ile Ala Phe Val Val Val Asn Ile Asn Ile Asn Tyr Arg Arg Pro Ala
    50                  55                  60

Val Leu Ser Asp Leu Leu Thr Ile Thr Ser Gln Leu Gln Gln Leu Asn
65                  70                  75                  80

Gly Lys Ser Gly Ile Leu Ser Gln Val Ile Thr Leu Glu Pro Glu Gly
                85                  90                  95

Gln Val Val Ala Asp Ala Leu Ile Thr Phe Val Cys Ile Asp Leu Lys
            100                 105                 110

Thr Gln Lys Ala Leu Ala Leu Glu Gly Glu Leu Arg Glu Lys Leu Glu
        115                 120                 125

Gln Met Val Lys
    130

<210> SEQ ID NO 2
<211> LENGTH: 707
<212> TYPE: PRT
<213> ORGANISM: Micrococcus luteus

<400> SEQUENCE: 2

Met Thr Val His Glu Lys Leu Ala Pro Gln Ser Pro Thr His Ser Thr
1               5                   10                  15

Glu Val Pro Thr Asp Val Ala Glu Ile Ala Pro Glu Arg Pro Thr Pro
            20                  25                  30

Gly Ser Leu Asp Ala Ala Ala Leu Glu Glu Ala Leu Leu Gly Arg Trp
        35                  40                  45

Ala Ala Glu Arg Arg Glu Ser Arg Glu Leu Ala Lys Asp Pro Ala Leu
    50                  55                  60
```

```
Trp Arg Asp Pro Leu Leu Gly Met Asp Glu His Ala Arg Val Leu
 65                  70                  75                  80

Arg Gln Leu Gly Val Leu Val Glu Arg Asn Ala Val His Arg Ala Phe
                 85                  90                  95

Pro Arg Glu Phe Gly Gly Glu Asp Asn His Gly Gly Asn Ile Ser Ala
                100                 105                 110

Phe Gly Asp Leu Val Leu Ala Asp Pro Ser Leu Gln Ile Lys Ala Gly
            115                 120                 125

Val Gln Trp Gly Leu Phe Ser Ser Ala Ile Leu His Leu Gly Thr Ala
130                 135                 140

Glu His His Arg Arg Trp Leu Pro Gly Ala Met Asp Leu Ser Val Pro
145                 150                 155                 160

Gly Ala Phe Ala Met Thr Glu Ile Gly His Gly Ser Asp Val Ala Ser
                165                 170                 175

Ile Ala Thr Thr Ala Thr Tyr Asp Glu Ala Thr Gln Glu Phe Val Ile
                180                 185                 190

His Thr Pro Phe Lys Gly Ala Trp Lys Asp Tyr Leu Gly Asn Ala Ala
            195                 200                 205

Leu His Gly Arg Ala Ala Thr Val Phe Ala Gln Leu Ile Thr Gln Gly
    210                 215                 220

Val Asn His Gly Val His Cys Phe Tyr Val Pro Ile Arg Asp Glu Lys
225                 230                 235                 240

Gly Ala Phe Leu Pro Gly Val Gly Gly Glu Asp Asp Gly Leu Lys Gly
                245                 250                 255

Gly Leu Asn Gly Ile Asp Asn Gly Arg Leu His Phe Thr Gln Val Arg
                260                 265                 270

Ile Pro Arg Thr Asn Leu Leu Asn Arg Tyr Gly Asp Val Ala Glu Asp
            275                 280                 285

Gly Thr Tyr Ser Ser Pro Ile Ala Ser Pro Gly Arg Arg Phe Phe Thr
            290                 295                 300

Met Leu Gly Thr Leu Val Gln Gly Arg Val Ser Leu Ser Leu Ala Ala
305                 310                 315                 320

Thr Thr Ala Ser Phe Leu Gly Leu His Gly Ala Leu Ala Tyr Ala Glu
                325                 330                 335

Gln Arg Arg Gln Phe Asn Ala Ser Asp Pro Gln Arg Glu Glu Val Leu
                340                 345                 350

Leu Asp Tyr Gln Asn His Gln Arg Leu Ile Asp Arg Leu Ala Arg
            355                 360                 365

Ala Tyr Ala Asp Ala Phe Ala Ser Asn Glu Leu Val Val Lys Phe Asp
    370                 375                 380

Asp Val Phe Ser Gly Arg Ser Asp Thr Asp Val Asp Arg Gln Glu Leu
385                 390                 395                 400

Glu Thr Leu Ala Ala Ala Val Lys Pro Leu Thr Thr Trp His Ala Leu
                405                 410                 415

Asp Thr Leu Gln Glu Ala Arg Glu Ala Cys Gly Gly Ala Gly Phe Leu
            420                 425                 430

Ala Glu Asn Arg Val Thr Gln Met Arg Ala Asp Leu Asp Val Tyr Val
    435                 440                 445

Thr Phe Glu Gly Asp Asn Thr Val Leu Leu Gln Leu Val Gly Lys Arg
            450                 455                 460

Leu Leu Thr Asp Tyr Ser Lys Glu Phe Gly Arg Leu Asn Val Gly Ala
465                 470                 475                 480

Val Ser Arg Tyr Val Val His Gln Ala Ser Asp Ala Ile His Arg Ala
```

-continued

```
                485                 490                 495
Gly Leu His Lys Ala Val Gln Ser Val Ala Asp Gly Gly Ser Glu Arg
            500                 505                 510

Arg Ser Ala Asn Trp Phe Lys Asp Pro Ala Val Gln His Glu Leu Leu
            515                 520                 525

Thr Glu Arg Val Arg Ala Lys Thr Ala Asp Val Ala Gly Thr Leu Ser
    530                 535                 540

Gly Ala Arg Gly Lys Gly Gln Ala Ala Gln Ala Glu Ala Phe Asn Thr
545                 550                 555                 560

Arg Gln His Glu Leu Ile Glu Ala Ala Arg Asn His Gly Glu Leu Leu
                565                 570                 575

Gln Trp Glu Ala Phe Thr Arg Ala Leu Glu Gly Ile Thr Asp Glu Thr
            580                 585                 590

Thr Lys Thr Val Leu Thr Trp Leu Arg Asp Leu Phe Ala Leu Arg Leu
            595                 600                 605

Ile Glu Asp Asp Leu Gly Trp Phe Val Ala His Gly Arg Val Ser Ser
    610                 615                 620

Gln Arg Ala Arg Ala Leu Arg Gly Tyr Val Asn Arg Leu Ala Glu Arg
625                 630                 635                 640

Leu Arg Pro Phe Ala Leu Glu Leu Val Glu Ala Phe Gly Leu Glu Pro
                645                 650                 655

Glu His Leu Arg Met Ala Val Ala Thr Asp Ala Glu Thr Gln Arg Gln
            660                 665                 670

Glu Glu Ala His Ala Trp Phe Thr Ala Arg Arg Ala Ala Gly Glu Glu
            675                 680                 685

Pro Glu Asp Glu Lys Ala Val Arg Ala Arg Glu Lys Ala Ala Arg Gly
    690                 695                 700

Arg Arg Gly
705
```